(12) United States Patent
Behrendt et al.

(10) Patent No.: US 7,390,660 B2
(45) Date of Patent: Jun. 24, 2008

(54) METHODS FOR GROWING MAMMALIAN CELLS IN VITRO

(75) Inventors: Ulrich Behrendt, Sindelsdorf (DE); Horst Eberhardt, Penzberg (DE); Berthold Szperalski, Penzberg (DE)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

(21) Appl. No.: 10/376,392

(22) Filed: Mar. 3, 2003

(65) Prior Publication Data

US 2003/0175951 A1 Sep. 18, 2003

(30) Foreign Application Priority Data

Mar. 5, 2002 (EP) .................. 02004366

(51) Int. Cl.
*C12N 5/12* (2006.01)
*C12N 5/06* (2006.01)
(52) U.S. Cl. .................. 435/385; 435/358; 435/326
(58) Field of Classification Search .............. 435/325, 435/326
See application file for complete search history.

(56) References Cited

U.S. PATENT DOCUMENTS

| 5,328,844 | A | | 7/1994 | Moore | |
|---|---|---|---|---|---|
| 5,719,050 | A | * | 2/1998 | Hashimoto et al. | 435/69.1 |
| 6,458,565 | B1 | * | 10/2002 | Cunningham et al. | 435/70.3 |
| 6,900,056 | B2 | | 5/2005 | Lee et al. | 435/404 |
| 2002/0042132 | A1 | * | 4/2002 | Gardner et al. | 435/388 |
| 2003/0096402 | A1 | * | 5/2003 | Lee et al. | 435/325 |

FOREIGN PATENT DOCUMENTS

| JP | 405095783 A | * | 4/1993 | |
|---|---|---|---|---|
| WO | WO 93/00423 A1 | | 1/1993 | |
| WO | WO98/41611 | | 9/1998 | |
| WO | WO 01/94552 A2 | | 12/2001 | |

OTHER PUBLICATIONS

Chen et al., Biotechnol. Bioeng., 72, pp. 55-61 (2001).
Colosimo et al., BioTechniques, 29, pp. 314-331 (2000).
Comer et al., Cytotechnology, 3, pp. 295-299 (1990).
Glacken et al., Biotechnol. Bioeng., 28, pp. 1376-1389 (1986).
Hu et al., Dev. Biol. Stand., 66, pp. 279-290 (1987).
Irani et al., Biotechnol. Bioeng., 66, pp. 238-246 (1999).
Xie et al., Cytotechnology, 15, pp. 17-29 (1994).
Hassell et al., J. Cell Sci., 96, pp. 501-508 (1990).
Europa et al., Biotechnol. Bioeng., 67, pp. 25-34 (2000).
Altamirano et al., Biotechnol. Prog., 16, pp. 69-75 (2000).
Xie et al., Trends in Biotechnology, 15, pp. 109-113 (1997).
Akshay Goel, et al., Biotechnol. Prog 4, pp. 380-385 (1995).
Shimomura, Y. et al, *Abstract of the 53rd Congress of Japan Society of Nut. & Food Sci,* (1999) 57.
Faiz-ur-Rahman, A.T.M. et al, *Planta,* 118 (1974) 211-224.
Toftegaard Nielsen, T. et al, *Scan. J. Lab. Invest.,* 40 (1980) 575-580.
Zammit, V.A., *FEBS Letters,* 108 (1979) 193-196.
Hencsey, Z., et al., Acta Microbiol. Hung., 43, pp. 359-370 (1996).
Dhir, S., et al., Biotechnol. Bioeng., 67, pp. 197-205 (2000).
Miller, W.M., et al., Biotechnol. Bioeng., 67, pp. 853-871 (2000).
Pörtner, R., and Schäfer, T., J. Biotechnol., 49, pp. 119-135 (1996).
Simonson, L., et al., Cytobios, 77, pp. 159-165 (1994).
Kromenaker, S., and Srienc., F., J. Biotechnol., 34, pp. 13-34 (1994).

* cited by examiner

*Primary Examiner*—Nancy Vogel
(74) *Attorney, Agent, or Firm*—George W. Johnston; Patricia S. Rocha-Tramaloni; Gene J. Yao

(57) ABSTRACT

The invention relates to a method for reducing glucose consumption during cultivation of animal cells, which comprises cultivating animal cells in the presence of a bi- or tricarbonic acid or a salt thereof at a concentration of about 1 to 50 mmol/l.

6 Claims, No Drawings

METHODS FOR GROWING MAMMALIAN CELLS IN VITRO

FIELD OF THE INVENTION

The invention provides a method for reducing lactate formation and/or glucose consumption in mammalian cell cultures by the addition of a bi- or tricarbonic acid, e.g. citric acid.

BACKGROUND OF THE INVENTION

Optimization strategies of cell culture processes aim at maximizing the longevity of cell culture (Bibila, T. A., and Robinson, D. K., Biotechnol. Prog. 11 (1995) 1-13). The final integrated number of viable cells over cultivation time is often used as a measure of cultivation success and is positively correlated with product formation. As used herein, this integral is defined as CTI (CTI=Cell density Time Integral).

Lactate is a major waste product formed during the cultivation of mammalian cells. Under typical culture conditions, the cells consume glucose in great excess and metabolize it mainly to lactate. The accumulation of lactate affects cell growth, CTI and protein production adversely as a result of pH and/or pH adjustment by alkali (Chang, Y. H. D., et al., Biotechnol. Bioeng. 47 (1995) 319-326); Omasa, T., et al., Biotechnol. Bioeng. 39 (1992) 556-565 and Chen, K., et al., Biotechnol. Bioeng. 72 (2001) 55-62).

There have been a lot of attempts to reduce lactate formation. It was suggested by Glacken, M. W., et al., (Biotechnol. Bioeng. 28 (1986) 1376-1389); Hu, W. S., et al., (Dev. Biol. Stand. 66(1987) 279-290); and Xie, L., and Wang, D. I. C., Cytotechnology 15 (1994) 17-29) to grow mammalian cells at low glucose concentrations with dynamic controlled feeding with glucose. The idea was to achieve a metabolic shift from high glucose/lactate flux to a low glucose/lactate flux. However, such methods require adaptations of the cells and need carefully designed control mechanisms of feeding. They are therefore complicated and difficult to perform (U.S. Pat. No. 6,156,570).

Other methods for reducing lactate formation are based on genetic engineering means. One method is described by Chen, K., et al., Biotechnol. Bioeng. 72 (2001) 55-62) suggesting manipulation of the metabolic pathway for lactate in the mammalian cells by inactivation of at least one copy of lactate dehydrogenase genes in the cells. Another method is described by Irani, N., et al., (J. Biotechnol. 66 (1999) 238-246), which introduces a pyruvate carboxylase gene into the host cell genome. It is assumed that the conversion of pyruvate to lactate is reduced and therefore the longevity of the cell culture is improved.

The addition of ferric citrate as a substituent for transferring in serum-free media for the cultivation of mammalian cells has been known for a long time (cf., e.g., Toyoda, K., and Inouye, K., Agric. Biol. Chem. 55 (1991) 1631-1633; Franek, F., and Dolnikova, J., Cytotechnology 7 (1991) 33-38; Kovar, J., and Franek, F., Exp. Cell Res. 182 (1989) 358-369; Schneider, Y. J., J. Immunol. Meth. 116 (1989) 65-77; and Kovar, J., Hybridoma 7 (1988) 255-263).

SUMMARY OF THE INVENTION

It has surprisingly been found that the addition of one or more bi- or tricarbonic acids inhibits the consumption of glucose and/or the formation of lactate from glucose considerably and therefore, improves cell density and cell viability during mammalian cell cultivation. Based on these findings, the yield of a protein of interest (POI) which is produced by such a cell cultivation increases considerably using the method according to the present invention. Further, the addition of bi- or tricarbonic acid reduces the amount of alkali which is needed to maintain a constant pH value from about 50% to about 70%. Accordingly, the present invention relates to a method for reduction of glucose consumption and/or lactate production during cultivation of animal cells in vitro. The cultivation is performed in the presence of one or more bi- or tricarbonic acids or their salts, such as oxoglutaric acid, succinic acid, fumaric acid, malic acid, ketoglutaric acid or citric acid or combinations thereof at a concentration of about 1 to 50 mmol/l. Specifically, where the di- or tricarbonic acid or salt is citric acid or citrate, this amount of citric acid or citrate is not bound in chelate complex with iron or another transition metal ion.

In a preferred embodiment of the invention, the animal cells are mammalian cells, preferably hybridoma or myeloma cells, CHO, NS0, BHK, or HeLa cells which produce monoclonal antibodies or proteinaceous hormones.

In a further preferred embodiment of the invention, the cells are cultivated in a fed batch, batch perfusion, dialysis, solid state, or continuous fermentation, preferably over a time period of 10 to 20 days.

DETAILED DESCRIPTION OF THE INVENTION

According to the invention, the specific rate of glucose consumption ($\mu g/10^6$ cells×day) is reduced to at least about 40%, preferably from about 40 to about 60%, in relation to a fermentation process using a method in which no uncomplexed citrate is present. The specific rate of lactate production ($\mu g/10^6$ cells×day) is reduced to at least about 50%, preferably from about 50 to about 70%, in relation to a fermentation process using a method in which no uncomplexed citrate is present.

Accumulation of lactate in the cell culture medium can inhibit cell growth and the POI production during cell cultivation. The growth-inhibitory lactate concentration varies with the cell line and the process. The lactate concentration after a certain time in a cultivation process is a result of the specific production rate of lactate and the CTI. This invention reduces the specific production rate of lactate, so that the period prolongs before the inhibitory concentration takes place, or in the best case, the concentration of lactate stays below the inhibitory concentration. However, this invention results in considerable increase of the CTI during the cultivation.

Cultivation of the cells is performed in a production dimension, i.e., in volumes of 10-10,000 l bioreactors. Such methods are described, for example, in Bibila, T. A., and Robinson, D. K., Biotechnol. Prog. 11 (1995) 1-13.

Preferably, the fermentation medium is a serum-free medium. Such media are widely described in the state of the art (see e.g. Murakami, H., Monoclonal Antibodies: Production and Application (1989) 107-141).

Bi- and tricarbonic acids are preferably added as an alkali metal or alkaline metal salt or as free acid at a concentration of about 1 to 50 mmol/l. This acid is preferably not bound to a chelate complex with iron or another transition metal. However, the medium may preferably contain an additional amount of a bi- and tricarbonic acid or a citrate salt thereof in a chelate complex with iron, which is added as an iron source of the serum-free medium. As previously stated, iron citrate is widely known as an additive to serum-free media as iron source should be, for example, transferrin.

The term "complexed bi- and tricarbonic acid" means an aqueous solution of stoichiometric amounts of the acid and iron ions which leads to complex formation within the law of mass action.

POI refers to any protein for which expression is desired. Preferably the term encompasses any recombinant form of a desired protein. Such proteins of interest are, for example, protein hormones like erythropoietin, or antibodies and the like. Such recombinant proteins are reviewed by, e.g., Hudson, P. J., and Souriau, C., Expert. Opin. Biol. Ther. 1 (2001) 845-855).

The mammalian cells are preferably recombinant cell lines like CHO cells or hybridoma or which myeloma cells are transformed with expression vectors capable of expressing such a POI. Such methods are well known in the art and reviewed by, e.g., Colosimo, A., et. al., Biotechniques 29 (2000) 314-331).

Fermentation in fed batch mode is preferably performed in stirred bioreactors for 4 to 10 days. The cell density is preferably between about 0.2 to about $10 \times 10^6$ cells/ml. $PO_2$ is preferably between about 15 to about 30% and pH between about 6.9 to about 7.3.

Fermentation in dialysis mode (Comer, M. J., et. al., Cytotechnology 3 (1990) 295-299) can be performed in stirred dialysis bioreactors for about 12 to about 16 days. The cell density is preferably between about 0.2 to about $30 \times 10^6$ cells/ml, $PO_2$ between about 15 to about 30% and pH between about 6.9 to about 7.3.

A common serum-free fermentation medium is used and a solution of concentrated nutrients is used for feeding.

The following examples and references are provided to aid the understanding of the present invention, the true scope of which is set forth in the appended claims. It is understood that modifications can be made in the procedures set forth without departing from the spirit of the invention.

EXAMPLE 1

The cells of a myeloma cell line (Sp2/0) were thawed and expanded up to 2 L in spinner flasks over a period of approximately 14 days for the inoculation of a 10 L bioreactor. After 2 to 4 days the cells were split or transferred to a 100 L bioreactor and further cultivated for 2 to 4 days. The 100 L bioreactor served as inoculum for the 1000 L production bioreactor. For each inoculum step a starting cell density of about 0.2 to about $0.4 \times 10^6$ viable cells per mL was used.

The production bioreactor ran in a dialysis mode. The bioreactor was a stirred tank reactor with a working volume of about 900 to about 1300 L. Aeration was performed by sparging. The following process parameters were controlled: pH, temperature, $pO^2$, pressure and agitation rate. The bioreactor was equipped for dialysis mode with hollow fibre cartridges. The cartridges were connected to an external loop with a dialysis medium reservoir. The dialysis of the culture was started 2 to 4 days after inoculation. During fermentation the reservoir was repeatedly filled up with fresh dialysis medium. Some medium components were fed as separate sterile solutions to the bioreactor. These comprise glucose, amino acids, vitamins, and trace elements.

Fermentation was terminated after a maximum of 16 days.

The citrate was added to the fermentation medium and to the dialysis medium.

Results of Example 1

Tables 1 and 2 show the specific consumption rate of glucose and the CTI of runs with and without the addition of citrate (similar results can be found if fumarate is used). The fermentations were performed in the dialysis mode at the 1000 L scale. The addition of citrate to the media reduced the specific consumption rate for glucose about 44% and increased the CTI to about 205%. At the same time the specific production rate for lactate was reduced to about 40% (Tables 3 and 4).

During fermentation the specific production rate of the POI were nearly constant, therefore the amounts of POI comparatively increased with the CTI.

TABLE 1

Fermentations In Dialysis Mode Without Addition Of Citrate

| Run No. | Specific consumption rate of glucose µg/$10^6$ cells x day | CTI Relative units |
|---|---|---|
| 1 | 663 | 134 |
| 2 | 873 | 98 |
| 3 | 776 | 96 |
| 4 | 736 | 100 |
| 5 | 1424 | 72 |
| Mean: | 894 | 100 |

TABLE 2

Fermentations In Dialysis Mode With Addition Of 2.4 Mmol/L Citrate

| Run No. | Specific consumption rate of glucose µg/$10^6$ cells x day | CTI Relative units |
|---|---|---|
| 6 | 705 | 142 |
| 7 | 351 | 262 |
| 8 | 429 | 219 |
| 9 | 549 | 195 |
| 10 | 481 | 208 |
| 11 | 355 | 275 |
| 12 | 535 | 213 |
| 13 | 537 | 128 |
| 14 | 519 | 215 |
| 15 | 578 | 192 |
| Mean: | 504 | 205 |

By addition of citrate to the fermentation medium, the amount of alkali which is required to adjust a constant pH value during the cultivation was reduced to about 34% of the control (Tables 3 and 4).

TABLE 3

Fermentations In Dialysis Mode Without Addition Of Citrate

| Run No. | Specific production rate of lactate µg/$10^6$ cells x day | Alkali Addition Relative units |
|---|---|---|
| 1 | 506 | 110 |
| 2 | 746 | 111 |
| 3 | 574 | 59 |
| 4 | 595 | 77 |
| 5 | 1064 | 144 |
| Mean: | 697 | 100 |

TABLE 4

Fermentations In Dialysis Mode With Addition Of 2.4 Mmol/L Citrate

| Run No. | Specific production rate of lactate µg/$10^6$ cells x day | Alkali addition Relative units |
|---|---|---|
| 6 | 491 | 107 |
| 7 | 176 | 18 |

TABLE 4-continued

Fermentations In Dialysis Mode With Addition Of 2.4 Mmol/L Citrate

| Run No. | Specific production rate of lactate μg/10⁶ cells x day | Alkali addition Relative units |
|---|---|---|
| 8 | 200 | 19 |
| 9 | 320 | 13 |
| 10 | 241 | 40 |
| 11 | 200 | 17 |
| 12 | 284 | 15 |
| 13 | 338 | 8 |
| 14 | 259 | 55 |
| 15 | 307 | 46 |
| Mean: | 282 | 34 |

EXAMPLE 2

The cells of a myeloma cell line were thawed (Sp2/0) and expanded up to 2 L in spinner flasks for the inoculation of a 10 L bioreactor.

The production bioreactor ran in a fed batch mode. The bioreactor was a stirred tank reactor with a working volume of from about 9 to about 13 L. Aeration was performed by sparging. The following process parameters were controlled: pH, temperature, pO2, pressure and agitation rate. Feeding of the culture was started 2 to 4 days after inoculation. Components including glucose, amino acids, vitamins, and trace elements were fed as separate sterile solutions to the bioreactor.

Fermentation was terminated after maximum of 10 days.

Citrate was added to the fermentation medium and the feeding medium.

Results of Example 2

Tables 5 and 6 show the specific production rate and the CTI of runs with and without the addition of citrate. The fermentations were performed in the feed batch mode at the 10 L scale. The addition of citrate to the media reduced the specific consumption rate for glucose to about 56% and increased the CTI to about 341%. At the same time the specific formation rate for lactate reduced to about 48%. This demonstrates the inhibition of the metabolic flux from glucose through glycolysis by the addition of citrate.

TABLE 5

Fermentations In Fed Batch Mode Without Addition Of Citrate

| Run No. | Specific consumption rate of glucose μg/10⁶ cells x day | Specific production rate of lactate μg/10⁶ cells x day | CTI Relative units |
|---|---|---|---|
| 1 | 1206 | 670 | 84 |
| 2 | 939 | 509 | 84 |
| 3 | 779 | 527 | 104 |
| 4 | 703 | 471 | 140 |
| 5 | 1022 | 714 | 75 |
| 6 | 948 | 727 | 62 |
| 7 | 839 | 665 | 90 |
| 8 | 1233 | 867 | 86 |
| 9 | 912 | 612 | 90 |
| 10 | 967 | 668 | 184 |
| Mean: | 955 | 643 | 100 |

TABLE 6

Fermentations In Fed Batch Mode With Addition Of 2.4 Mmol/L Citrate

| Run No. | Specific consumption rate of glucose μg/10⁶ cells x day | Specific production rate of lactate μg/10⁶ cells x day | CTI Relative units |
|---|---|---|---|
| 11 | 443 | 230 | 478 |
| 12 | 715 | 392 | 321 |
| 13 | 451 | 304 | 224 |
| Mean: | 536 | 309 | 341 |

What is claimed is:

1. A method for reducing glucose consumption during cultivation of CHO, myeloma, or hybridoma cells, comprising cultivating CHO, myeloma, or hybridoma cells in culture medium in the presence of citric acid or citrate wherein said citric acid or citrate is maintained at a concentration of about 1 to 50 mmol/l during cultivation and wherein said citric acid or citrate is not bound in a chelate complex with iron or another transition metal ion.

2. The method of claim 1, wherein the cells are myeloma cells.

3. The method of claim 1, wherein the cells are hybridoma or CHO cells.

4. A method for reducing lactate production during cultivation of CHO, myeloma, or hybridoma cells, comprising cultivating CHO, myeloma, or hybridoma cells in culture medium in the presence of citric acid or citrate wherein said citric acid or citrate is maintained at a concentration of about 1 to 50 mmol/l during cultivation and wherein said citric acid or citrate is not bound in a chelate complex with iron or another transition metal ion.

5. The method of claim 4, wherein the cells are myeloma cells.

6. The method according to claim 4, wherein the cells are hybridoma or CHO cells.

* * * * *